United States Patent [19]
Graf et al.

[11] Patent Number: 5,645,588
[45] Date of Patent: Jul. 8, 1997

[54] GRAFT ATTACHMENT DEVICE

[75] Inventors: Ben K. Graf, Madison, Wis.; Thomas D. Rosenberg, Salt Lake City, Utah; Joseph H. Sklar, Longmeadow; Michael C. Ferragamo, No. Dighton, both of Mass.

[73] Assignee: Acufex Microsurgical, Inc., Mansfield, Mass.

[21] Appl. No.: 541,394

[22] Filed: Oct. 10, 1995

Related U.S. Application Data

[60] Continuation of Ser. No. 162,509, Dec. 3, 1993, abandoned, which is a division of Ser. No. 16,411, Feb. 11, 1993, Pat. No. 5,306,301.

[51] Int. Cl.$^6$ .................................................. A61F 2/08
[52] U.S. Cl. ................................................ 623/13; 606/151
[58] Field of Search ...................................... 623/12, 13, 16, 623/18; 606/72, 73, 99, 105, 148, 151, 232, 228; 600/37

[56] References Cited

U.S. PATENT DOCUMENTS

| | | | |
|---|---|---|---|
| 65,499 | 6/1867 | Miller | 606/232 X |
| 3,683,422 | 8/1972 | Stemmer et al. | 623/18 X |
| 3,896,500 | 7/1975 | Rambert et al. | 623/13 |
| 4,210,148 | 7/1980 | Stivala | 128/335 |
| 4,400,833 | 8/1983 | Kurland | 623/18 X |
| 4,409,974 | 10/1983 | Freedland | 128/92 |
| 4,584,722 | 4/1986 | Levy et al. | 623/13 |
| 4,708,132 | 11/1987 | Silvestrini | 128/92 |
| 4,744,793 | 5/1988 | Parr et al. | 623/13 |
| 4,772,286 | 9/1988 | Goble et al. | 623/13 |
| 4,773,910 | 9/1988 | Chen et al. | 623/13 |
| 4,870,957 | 10/1989 | Goble | 128/69 |
| 4,896,668 | 1/1990 | Popoff et al. | 606/74 |
| 4,979,956 | 12/1990 | Silvestrini | 623/13 |
| 4,997,433 | 3/1991 | Goble et al. | 606/64 |
| 5,037,422 | 8/1991 | Hayhurst et al. | 606/72 |
| 5,046,513 | 9/1991 | Gatturna et al. | 128/898 |
| 5,062,843 | 11/1991 | Mahony | 606/73 |
| 5,116,373 | 5/1992 | Jakob et al. | 623/13 |
| 5,139,520 | 8/1992 | Rosenberg | 623/13 |
| 5,147,362 | 9/1992 | Goble | 606/72 |
| 5,152,790 | 10/1992 | Rosenberg et al. | 623/13 |
| 5,203,787 | 4/1993 | Noblitt et al. | 606/232 |
| 5,282,809 | 2/1994 | Kammerer et al. | 606/148 |
| 5,290,217 | 3/1994 | Campos | 600/37 |
| 5,362,294 | 11/1994 | Seitzinger | 600/37 |

FOREIGN PATENT DOCUMENTS

| | | | |
|---|---|---|---|
| 0464480 | 1/1992 | European Pat. Off. | 606/232 |
| 520177 | 12/1992 | European Pat. Off. . | |
| 2227175 | 7/1990 | United Kingdom | 623/11 |

OTHER PUBLICATIONS

Acufex Brochure, (1988).

*Primary Examiner*—David H. Willse
*Attorney, Agent, or Firm*—Fish & Richardson P.C.

[57] ABSTRACT

A graft attachment device having an elongated body with a leading end and a trailing end, each defining an element for carrying a filament such as a suture. The body further defines at least one element for attaching to the body either a graft or a graft connection element which is in turn connected to the graft. The element for attaching enables the body to rotate relative to the graft from an initial insertion position, along an axis substantially parallel to the graft, to a final fixation position transverse to the graft to secure the graft relative to a bone.

11 Claims, 9 Drawing Sheets

GRAFT ATTACHMENT DEVICE

This is a continuation of application Ser. No. 08/162,509 filed Dec. 3, 1993, now abandoned; which is a divisional of application Ser. No. 08/016,411 filed on Feb. 11, 1993, now U.S. Pat. No. 5,306,301.

FIELD OF THE INVENTION

This invention relates to a device and method for securing tissue within a patient and more particularly to fixating a graft relative to a bone.

BACKGROUND OF THE INVENTION

An increasing number of surgical techniques are now performed arthroscopically. One type of arthroscopic procedure reconstructs the anterior cruciate ligament (ACL) in the knee. Several ACL reconstruction techniques are described in U.S. Pat. No. 5,139,520 (Rosenberg), which is incorporated herein by reference. The replacement ACL graft is selected, according to surgeon preference, from a portion of a patellar tendon having a bone block or plug at each end, a semitendinosus graft which is whip-stitched with suture at each end, a fully prosthetic device, or a combination of artificial and natural material such as a ligament augmentation device (LAD) to which tissue is sutured. The term "graft" is used herein to encompass all of these tissue replacement items.

Presently, different attachment devices are used to secure those various grafts in position. The bone block portions of patellar tendon grafts are typically fixated in the femoral tunnel or channel using a headless interference screw. If the graft bone block or the femoral bone lacks sufficient structural integrity, however, this procedure may not be advisable. Further, there is a possibility that the screw could shift in position a number of months or years after implantation which may interfere with joint movement or integrity. Additionally, the screw physically blocks bone tissue from growing into the graft to naturally secure it within the femur.

Semitendinosus grafts are typically fixated using a circular button-type fixation device which is implanted through the outer side (lateral) surface of the leg above the knee. This implantation requires an ancillary lateral incision through the skin and quadriceps muscle which increases the trauma to the leg and is, at the least, cosmetically undesirable. Moreover, time must be taken during the surgical procedure to tie sutures from the graft to the button-type device, which extends the length of the overall operation.

SUMMARY OF THE INVENTION

Therefore, it is an object of the present invention to provide a simple, one-piece graft attachment device and method of installing same.

It is a further object of the invention to provide secure fixation of a graft with minimal trauma to the patient.

A still further object is to obviate the need for a bone block or other hard section attached to the graft.

Yet another object is to enable tying sutures to an attachment device prior to and independent of graft installations, or to eliminate the need for tying sutures to the device altogether.

A further object is to minimize interference with bone tissue regrowth after implantation.

This invention features a graft attachment device having an elongated body with a leading end and trailing end, each defining means for carrying a filament such as a suture. The body further defines at least one means for attaching to the body either (1) a graft or (2) a graft connection element which is in turn connected to the graft. The means for attaching is disposed between the leading and trailing means for carrying filament and enables the body to rotate relative to the graft from an initial insertion position, along an axis substantially parallel to the graft, to a final fixation position transverse to the graft to secure the graft relative to a bone.

In one embodiment, each means for carrying is a hole defined by the elongated body to carry a lead suture and a trailing suture as the filaments. The means for attaching can be selected from the group of a single opening, two adjacent openings, or a bracket extending from the lower surface of the elongated body and defining an opening. The openings accomodate sutures or a ligament augmentation device threaded through the opening or openings. Alternatively, a graft itself is threaded through the openings. In a still further embodiment, a sling member serves as the graft connection element and is secured as an endless loop of polyester tape material inserted through the means for attaching.

This invention further features a method of attaching a graft to the bone using such a graft attachment device. Method includes forming a socket in a bone such as a femur to accomodate an end of the graft, the socket having an opening at one end and a floor at its opposite end. A passage is formed from the floor of the socket to the opposite side of the bone, the passage having a width at least as large as the maximum width of the graft attachment device. The graft is secured to the means for attaching, and the lead and trailing filaments are inserted through the passage. The lead filament is pulled until the elongated body of the graft attachment device emerges from the passage. The elongated body is then rotated by pulling on the trailing filament to rotate the body from an initial insertion position substantially parallel to the graft to a final fixation position transverse to the graft. The elongated body is then seated against the surface of the bone by pulling on the graft to fixate the graft to the bone.

In one embodiment, a socket is formed to a depth substantially equal to a desired insertion depth for the graft plus one-half of the maximum length of the graft attachment device. The method further includes selecting perceptively different sutures to serve as the lead and trailing filaments, and disengaging the lead and trailing filaments from the elongated body before completing the seating of the elongated body against the bone.

BRIEF DESCRIPTION OF THE DRAWINGS

Other objects, features and advantages will occur from the following description of preferred embodiments and the accompanying drawings, in which.

DETAILED DESCRIPTION OF THE PREFERRED EMBODIMENTS

A graft attachment device 10 according to the present invention is illustrated in FIGS. 1-4 having an elongated body 12, an upper surface 14, a lower surface 16, a maximum width 18, and a maximum length 20. The elongated body 12 has a leading end 22 and a trailing end 24, each of which define holes 26, 28, respectively. Holes 26, 28 carry lead and trailing filaments as described below. The elongated body 12 further defines openings 30, 32 through which a graft is attached directly or indirectly using sutures or a sling, as described in more detail below.

In one construction, the elongated body 12 is a rectangular, bar-shaped member formed of surgical quality stainless steel. Other biocompatible materials are acceptable, such as a Delrin polymer available from Du Pont or a bioabsorbable material such as polylactic acid, polyglycolic acid disclosed in U.S. Pat. No. 3,739,773 (Schmitt et al.), or copolymers disclosed in U.S. Pat. Nos. 4,300,565 (Rosensaft et al.) and 4,429,080 (Casey et al.), all of which are incorporated herein by reference. A combination of absorbable and non-absorbable materials to form a partially absorbable material implant can also be utilized. A polymer such as polylactic acid is preferred for its slower absorption rate and therefore longer retention of structural integrity.

In this construction, device 10 has a width of 4 mm, a length of 12 mm, holes 26, 28 of 0.062 inch and openings 30, 32 of 0.78 inch. All edges are rounded to avoid chafing of suture or graft.

Figures 1, 2:
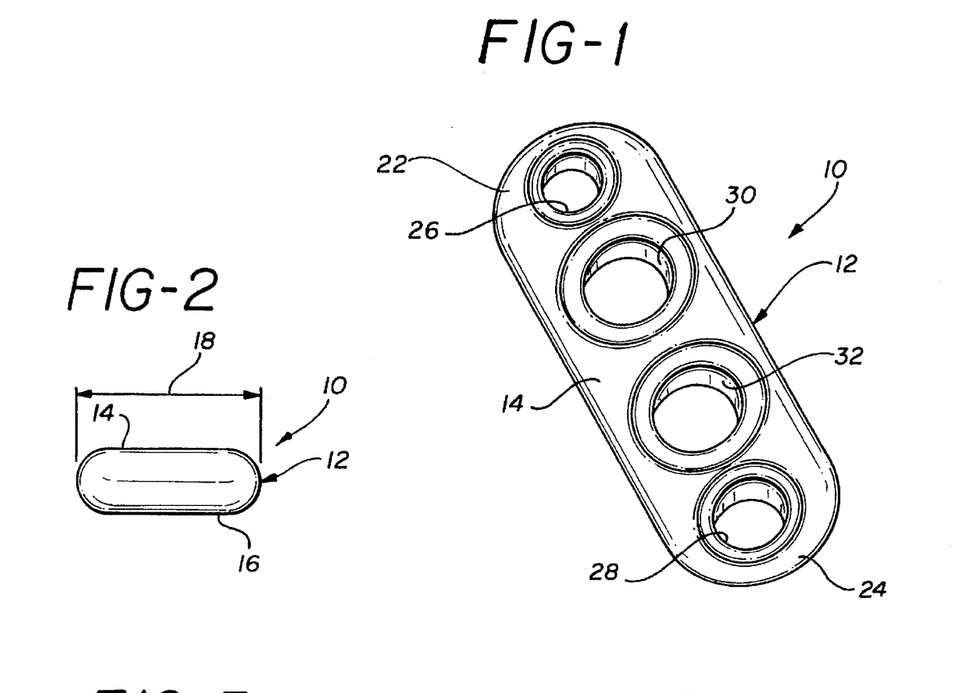
FIG. 1 is a top perspective view of a graft attachment device according to the present invention.
FIG. 2 is an end elevational view thereof.
Figure 3:
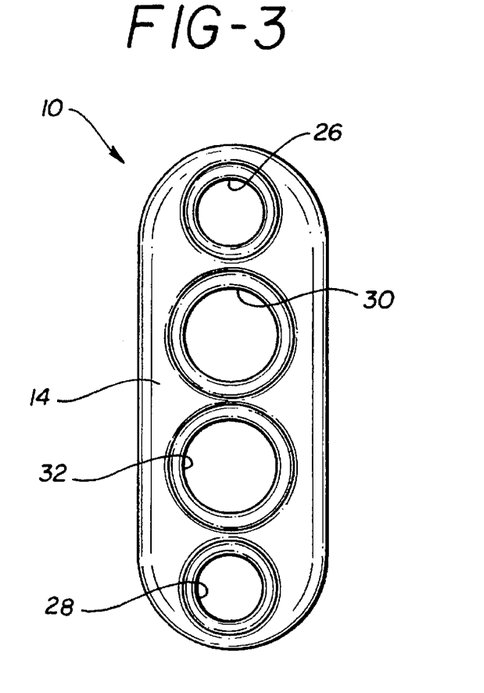
FIG. 3 is a top plan view thereof.
Figure 4:
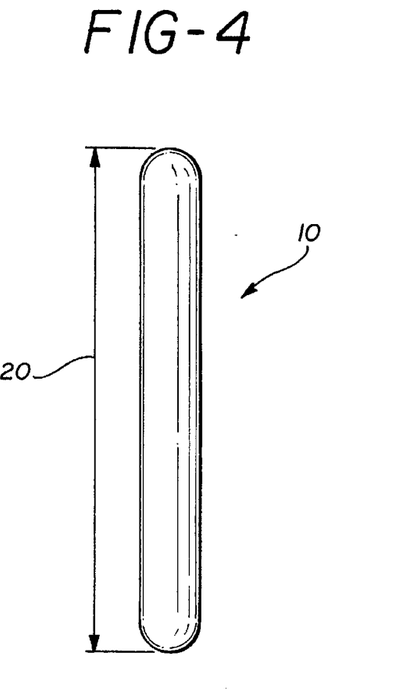
FIG. 4 is a side elevational view thereof.
Figure 5:
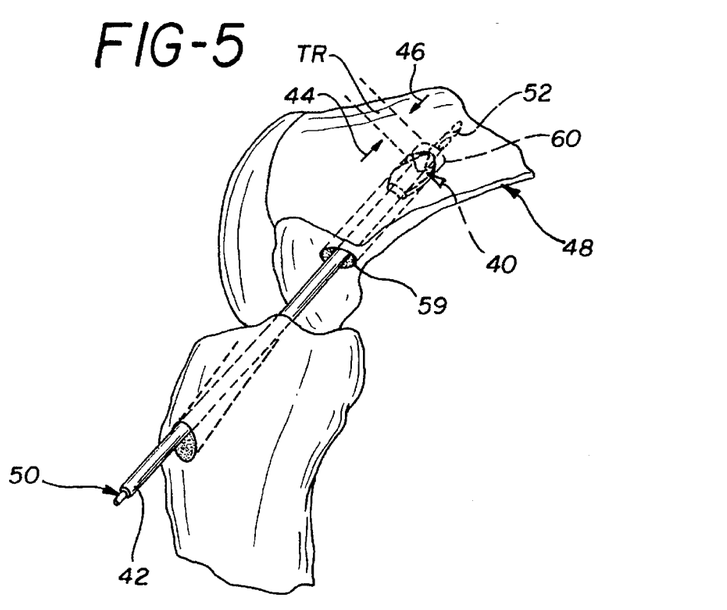
FIG. 5 is a schematic view of a deep femoral socket being formed according to present invention in a patient.

A method of using the graft attachment device is as follows. To reconstruct the anterior cruciate ligament (ACL), notchplasty is performed at the intercondylar notch as described in U.S. Pat. No. 5,139,520 (Rosenberg), incorporated herein by reference. A drill guide is used to form a tibial channel as described in the Rosenberg '520 patent; an adjustable drill guide as disclosed in U.S. Pat. No. 5,163,940 (Bourque) can also be used. The isometric position at the femoral surface is located, and a guide wire is drilled through the tibial channel and into the femur. A closed-end socket 40 having an opening 59 is then formed as illustrated in FIG. 5, using a drill 42 with an abbreviated drilling head as described in the Rosenberg '520 patent. Unlike conventional techniques, however, the femoral socket 40 is made deeper by the length TR indicated by arrows 44, 46. The total length of the socket 40 is the desired insertion distance for the graft, plus an additional distance equal to one-half of the length of the graft attachment device to accomodate a turning radius as described below. Semitendinosus grafts are preferably inserted at least 15 mm into the femur 48; a graft attachment device having a length of 12 mm would necessitate a length TR between arrows 44, 46 of an additional 6 mm.

Figure 6:
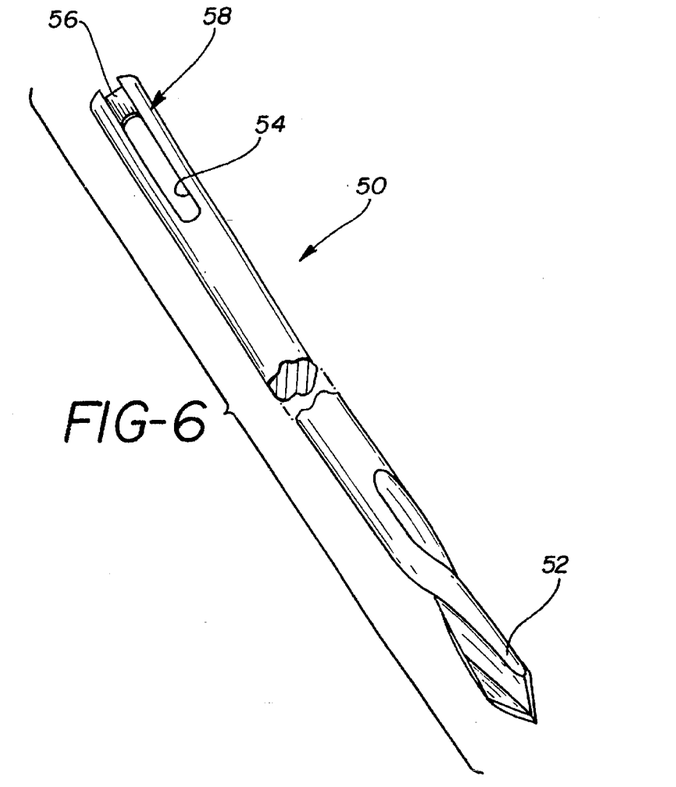
FIG. 6 is a partial perspective view of a drill-tipped passing pin used according to the present invention.

The drill 42 is shown extending over a passing pin instrument 50 having a double-fluted drill tip 52 as shown in greater detail in FIG. 6. Although a conventional drill-tipped guide wire can be used at this stage, the pin device 50 has a slot 54 and a groove 56 at its proximal end 58 for use as described below.

After the socket 40 is fully formed, the drill 42 is withdrawn, and the passing pin instrument 52 is advanced to the upper (anterolateral) femoral cortex beyond the floor 60 of the socket 40. At this stage, the pin instrument 50 can be rotated and extended further to pierce the quadriceps and skin; alternatively, the soft-tissue passage is accomplished later, as described in more detail below.

Figures 7A, 7B:
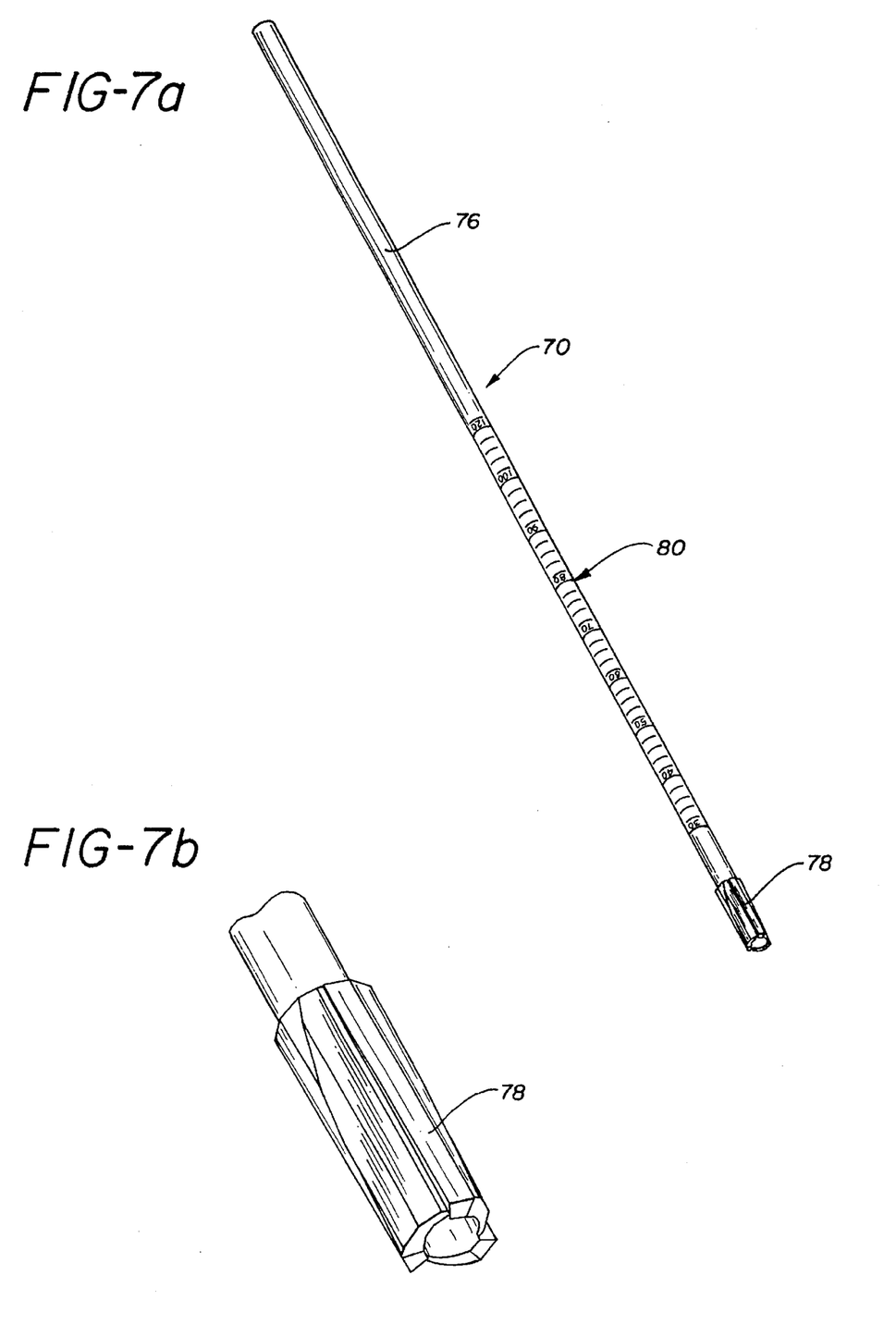
FIGS. 7a and 7b illustrate a cannulated drill bit.
Figure 8:
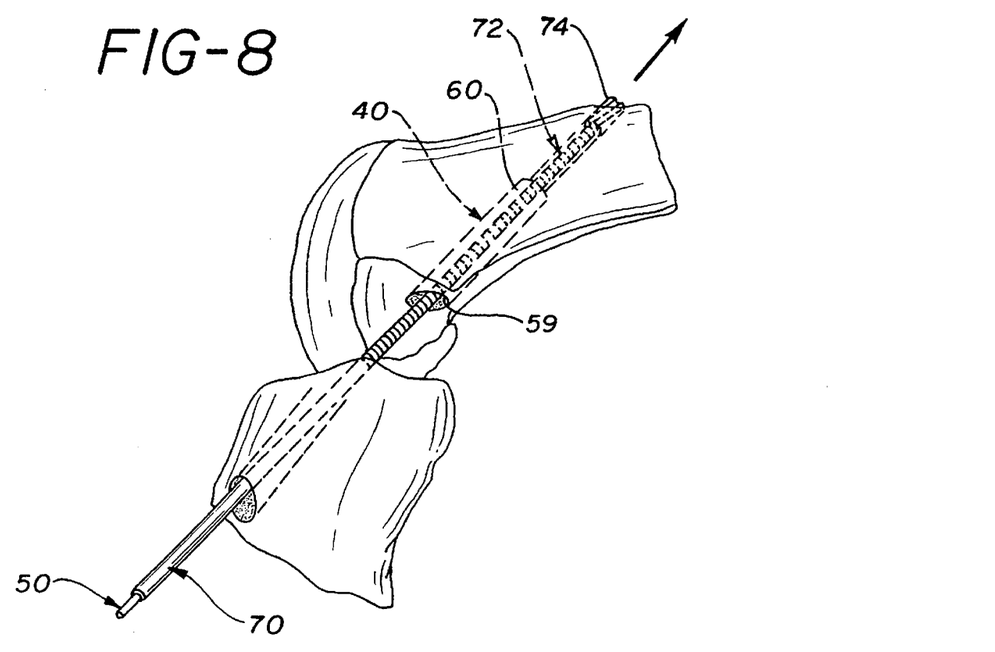
FIG. 8 illustrates the cannulated drill bit of FIGS. 7a, 7b being guided over the passing pin of FIG. 6 within the patient.

A cannulated drill 70, FIGS. 7a, 7b and 8, is then inserted over the pin instrument 50 to drill a passage 72 extending from the floor 60 to the upper cortex 74. The drill 70 includes a tubular shaft 76 and an enlarged drilling head 78. In one construction, the pin instrument 50 has an outer diameter of approximately 2.4 mm, and the drill 70 has an inner diameter of approximately 0.100 which is slightly greater than 2.4 mm. The shaft 76 has an outer diameter of 0.130, and the drilling head 78 has an outer diameter of 4.5 mm and a length of 0.440 inch, for use with a graft attachment device having a maximum width of 4 mm. The thin walls of shaft 76 are achieved using drawn tubing formed of 416 stainless steel and having a length of approximately 8 inches. Millimeter scale 80 is used to determine the total length TL, FIG. 11 of the socket 40 plus the passage 72.

Figure 7C:
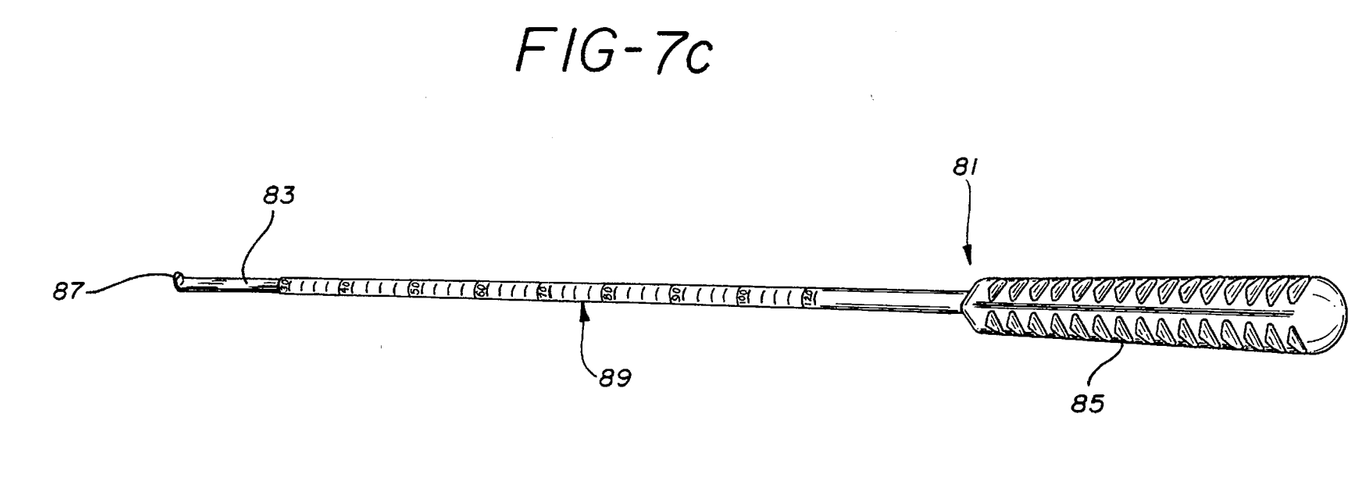
FIGS. 7c and 7d are schematic perspective views of a depth probe used in the present invention.
Figure 7D:
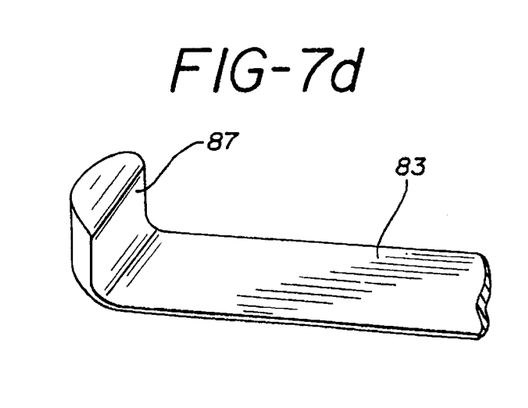
Figures 10, 11:
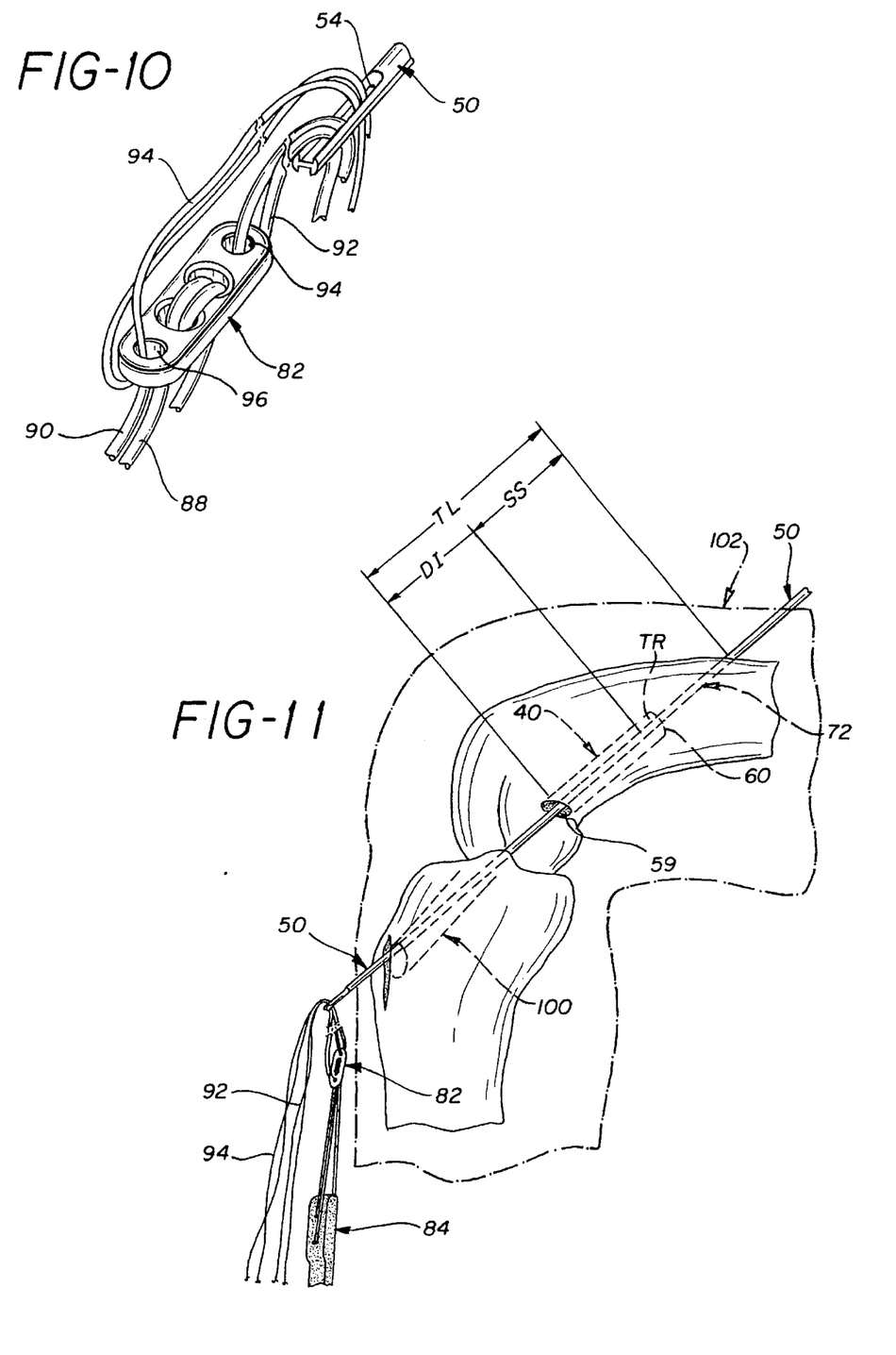
FIG. 10 shows lead and trailing sutures threaded through the proximal portion of the passing pin of FIG. 6.
FIG. 11 illustrates insertion of the lead and trailing filaments through the femoral passage.

Alternatively, a separate calibrated depth probe 81, FIGS. 7c and 7d, is inserted to accurately measure the total length. Probe 81 includes a shaft 83 attached at one end to a handle 85 and having a hook 87 at its opposite end for engaging the femoral cortex 74, FIG. 8. The total length TL, FIG. 11, is then read arthroscopically from millimeter scale 89. In one construction, probe 81 is approximately 13 inches in length, shaft 83 is 9 inches, and hook 87 is 0.160 inch.

Figure 9:
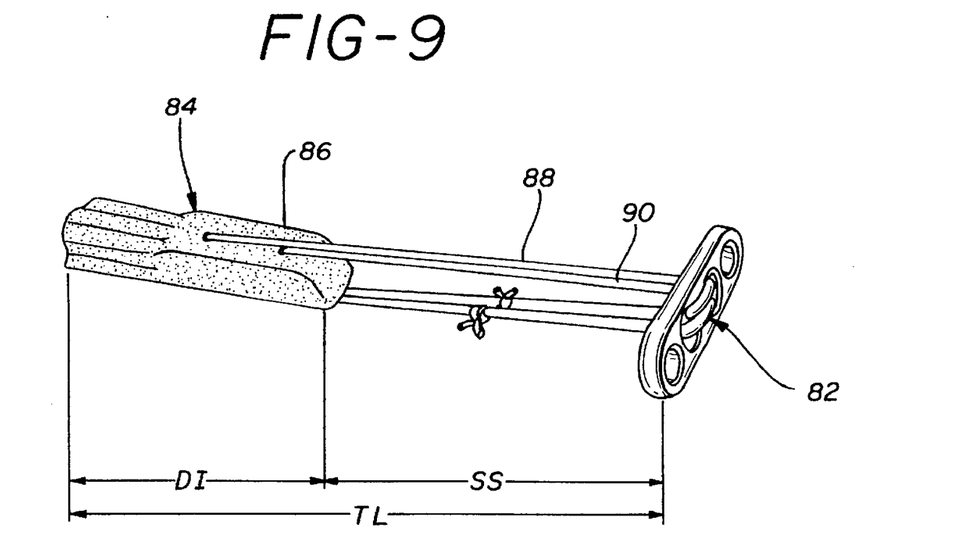
FIG. 9 is a schematic perspective view of a graft attachment device according to the present invention secured to a bone block of a patellar tendon graft by sutures.

The passage 72, FIG. 8, has a width at least as great as the maximum width of the selected graft attachment device 82, FIG. 9. The measured total length TL is illustrated in FIG. 9, which is the sum of the desired insertion length DI and the span of sutures SS. As illustrated, a patellar tendon graft 84 having a bone block 86 is connected to the graft attachment device 82 by sutures 88, 90 such as Ticron No. 5 sutures. Alternative graft connections are described below. One advantage of the present invention is that the linkage between the graft 84 and the graft attachment device 82 can be performed by surgical assistants immediately after the graft is harvested, and independently of the above-described drilling procedures.

A lead suture 92 and a trailing suture 94 are then threaded through filament carrying holes 94, 96, respectively, as shown in FIG. 10. It is preferable that the sutures 92, 94 be perceptively different from each other, such as by having different diameters, for example No. 5 Ticron for lead suture 92 and No. 2 Ticron for trailing suture 94. Alternatively, different colored filaments could be used. Moreover, metal wires or other filaments can be utilized instead of sutures.

After being looped through the graft attachment device 82, the lead and trailing sutures 92, 94 are threaded through the slot 54 of the passing pin instrument 50.

Figure 12A:
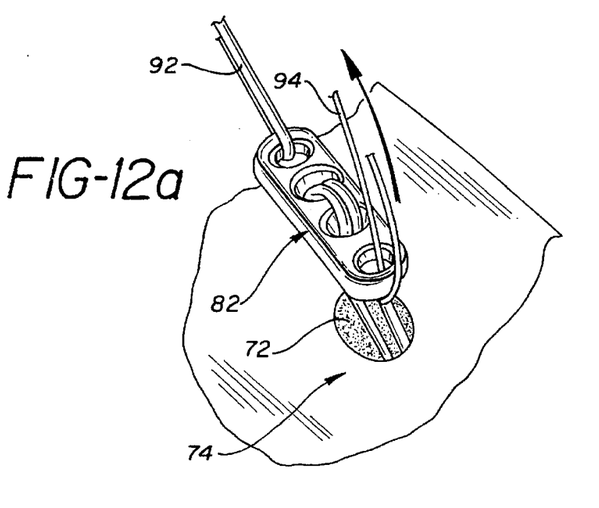
FIG. 12a and 12b schematically show rotation of the graft attachment device from an insertion position to a final fixation position.
Figure 12B:
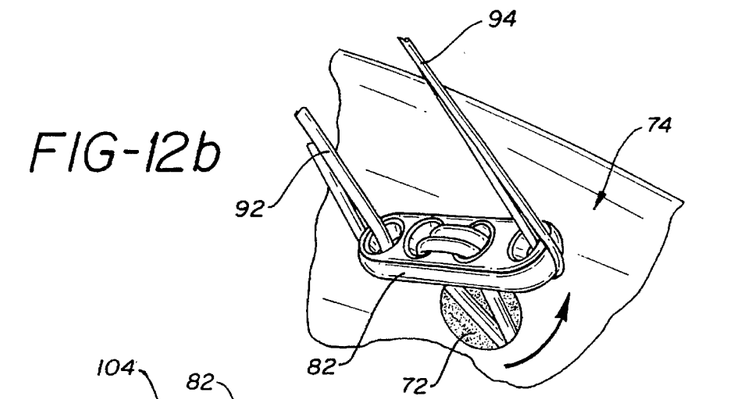
Figure 13:
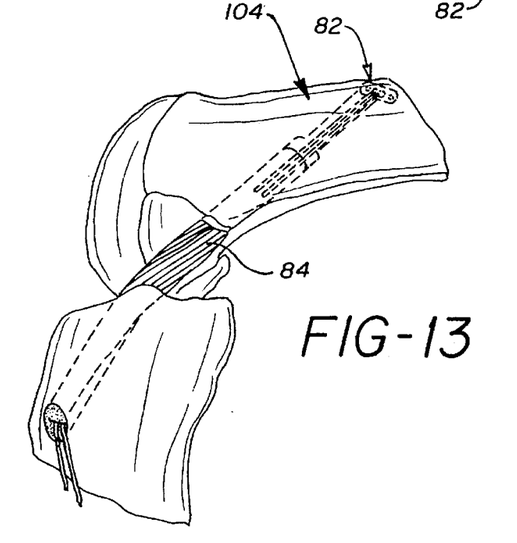
FIG. 13 illustrates complete seating of the graft attachment device against the upper surface of the femur to secure the patellar tendon graft in position.

The passing pin instrument 50 is then inserted through the tibial channel 100, the femoral socket 40, the femoral passage 72, and then through the quadriceps and skin 102 as shown in FIG. 11. Preferably, an indicator line has been placed on the graft 84 using a surgical marker to indicate the total depth of the femoral socket 60. When the lead and trailing sutures 92, 94 are then withdrawn beyond skin 102, the lead suture 92 is pulled as indicated in FIG. 12a until the graft attachment device 82 emerges from the passage 72 where it terminates at upper femoral cortex 74. The indicator line which has been placed on the graft is viewed arthroscopically at femoral socket entrance 59, FIG. 11, which indicates that the graft has advanced beyond the desired insertion length and into the turning radius space TR. Therefore, the device 82 has sufficient clearance to be rotated when trailing suture 94 is pulled as shown in FIG. 12b. The graft 84 is then pulled at its opposite end to seat the device 82 as shown in FIG. 13 against the cortex 74. The tibial end of the graft is thereafter secured conventionally.

Figure 14:
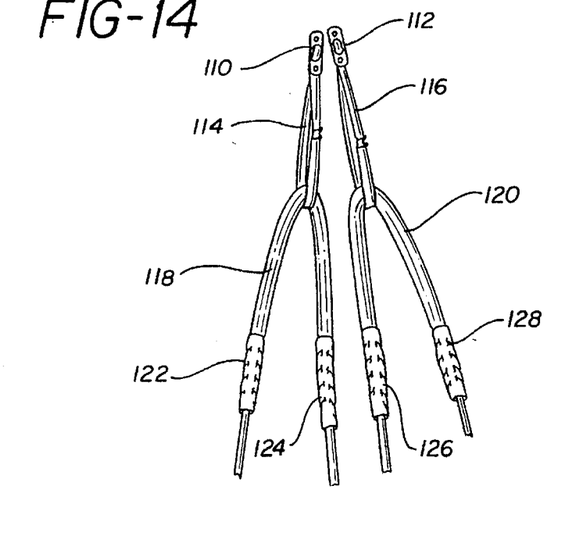
FIG. 14 illustrates an alternative arrangement using slings to carry semitendinosus grafts.

Several modifications according to the present invention are illustrated in FIG. 14. Instead of tying a graft directly to graft attachment devices 110, 112, slings 114, 116 of one-quarter inch polyester tape are tied to form an endless loop having a length of the suture span SS. Suitable polyester tapes include Mercelene tape available from Ethicon and Dacron available from Davis & Geck, each having a width of one-quarter inch and a narrower thickness. Alternatively, a set of graft attachment devices having different preformed endless loops can be provided to the surgeon for selection of the appropriate length. The slings 114, 116 accomodate semitendinosus grafts 118, 120 which are simply looped over the slings without further attachment. The whip-stitched ends 122, 124, 126 and 128 are used to secure the tibial end of the grafts after implantation.

Figure 15:
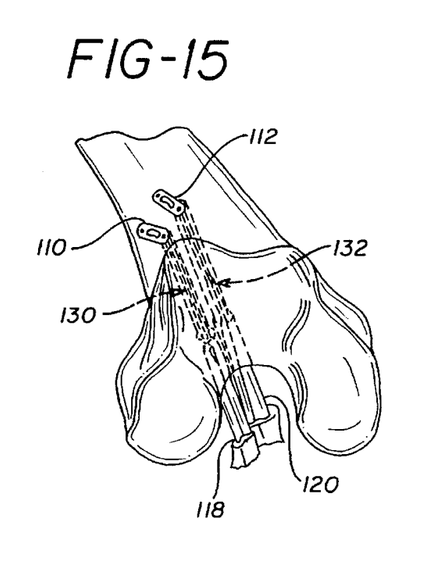
FIG. 15 shows an alternative technique in which two graft attachment devices are utilized, each associated with a different femoral channel.

FIGS. 14 and 15 further illustrate use of dual graft attachment devices according to the present invention, each placed in a separate femoral socket 130, 132. This arrangement decreases the load placed on each graft attachment device and dramatically increases the exposed surface area of the grafts 118, 120 to enhance bone tissue ingrowth about the grafts.

Figure 16:
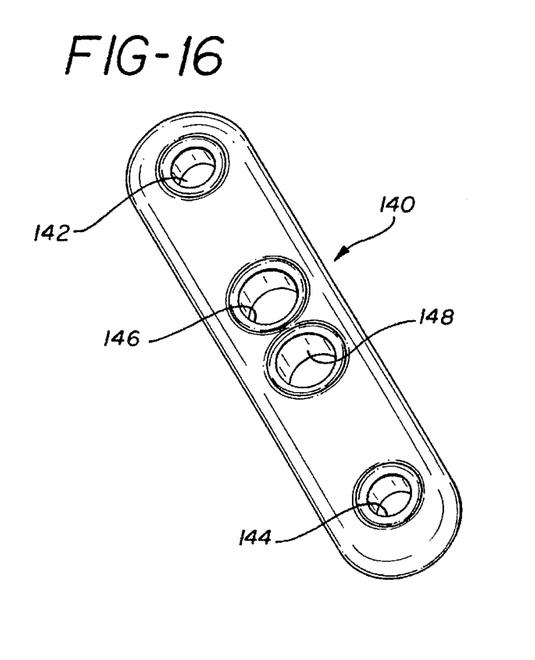
FIG. 16 is a perspective view of an alternative, elongated graft attachment device.

An alternative, elongated graft attachment device 140 is illustrated in FIG. 16. In one construction, the device 116 has a width of 4 mm (0.157 inch) with a length of 16.5 mm (0.650 inch). Holes 142, 144 have a diameter of 0.062 inch and carrying openings 146, 148 have a diameter of 0.78 inch. The device 140 has a thickness of 0.060 inch, and all edges are rounded.

Figure 17:
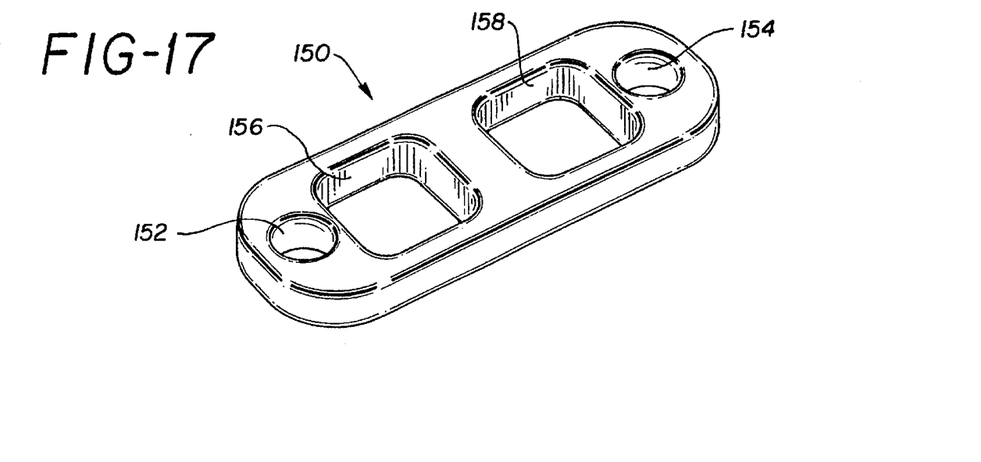
FIG. 17 is a schematic perspective view of yet another graft attachment device having enlarged openings through which a graft is threaded.

Alternative device 150, FIG. 17, has holes 152, 154 as previously described but has enlarged carrying openings 156, 158 through which the graft itself can be threaded. The graft can be a semitendinosus segment, or a ligament augmentation device (LAD), for example. One type of LAD is the Kennedy LAD available from Minnesota Mining and Manufacturing Company, Catalog Part No. 11331, having a width of 6 mm, and a length of 11 cm. The openings 156, 158 are approximately 4 mm in width, and the device 150 has a total width of 6 mm and a length of 15 mm.

Figure 18:
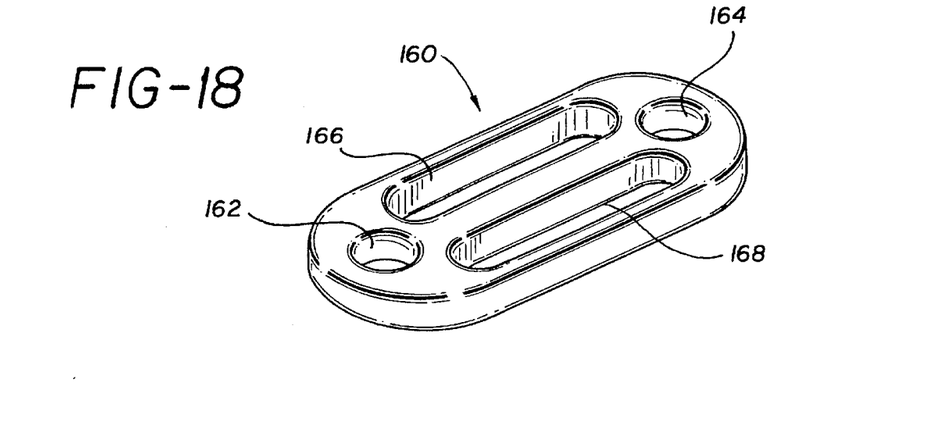
FIG. 18 is a schematic perspective view of a still further embodiment having dual elongated openings.

Another configuration is shown in FIG. 18 wherein device 160 has round holes 162, 164 and the elongated openings 166, 168 through which a LAD or sutures can be passed. The device 160 in one construction has a width of 6 mm, a length of 15 mm, and a thickness of 0.62 inch. The openings 166, 168 have a width of 0.05 inch (1.4 mm) and a length of 0.320 inch.

Figure 19:
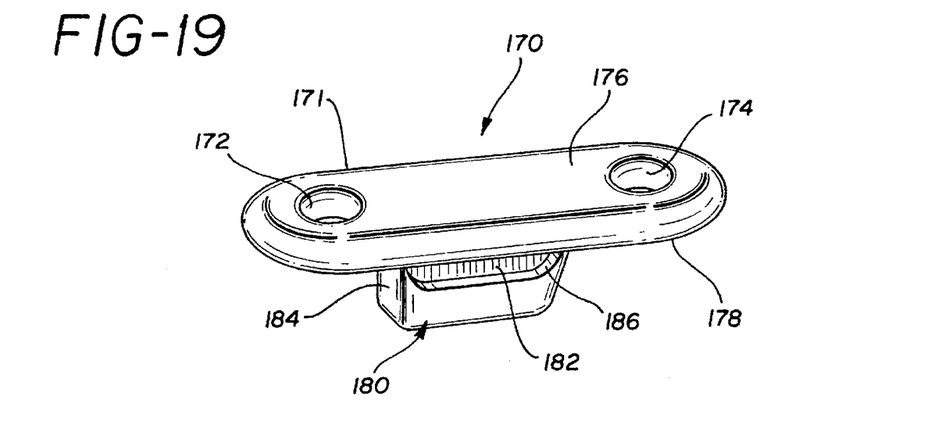
FIG. 19 is a schematic perspective view of a graft attachment device having a bracket attached to its lower surface.

A still further graft attachment device 170 according to the invention is illustrated in FIG. 19 having an elongated body 171 which defines lead and trailing filament holes 172, 174, an upper surface 176, and a lower surface 178. A bracket 180 extends downwardly from the lower surface 178 and defines an opening 182 through which the graft or graft connection element is threaded. In one construction, the opening 182 has a length of 0.236 inch and the legs 184, 186 of the bracket 180 are tapered at an 80 degree angle relative to the lower surface 178. Preferably, all edges are rounded.

This invention is not limited to ACL reconstruction. For example, a posterior cruciate ligament or other soft tissue can be reconstructed or fixated according to the present invention.

Although specific features of the invention are shown in some drawings and not in others, this is for convenience only as each feature may be combined with any or all of the other features in accordance with the invention.

Other embodiments will occur to those skilled in the art and are within the following claims.

We claim:

1. A graft attachment device for attaching an anterior cruciate ligament graft to a bone wherein a passage is drilled through the bone for attachment thereto, comprising:

an elongated body sized to pass through the passage in the bone and having an upper surface, a lower surface, a leading end, and a trailing end, each said end having a hole defined by said elongated body configured to carry a filament, and said body further defining two adjacent openings for attaching to said body one of the graft and a graft connection element, said two adjacent openings being disposed between said hole in said leading end and said hole in said trailing end and enabling said body to rotate relative to the graft from an initial insertion position, along an axis substantially parallel to the graft, to a final fixation position transverse to the graft to secure the graft relative to the bone;

filament releasably threaded through said holes defined in said leading end and said trailing end; and a graft connection element comprising a sling member, said sling member having a width sufficient to carry the graft during and after implantation.

2. The graft attachment device of claim 1 in which said filament comprises suture.

3. The graft attachment device of claim 1 in which said sling member is a loop of polyester tape material.

4. The graft attachment device of claim 1 wherein said filament comprising a lead suture releasably connected to said hole defined in said leading end and a trailing suture releasably connected to said hole defined in said trailing end, said lead and trailing sutures being perceptibly different from one another.

5. The graft attachment device of claim 4 in which said lead suture has a larger diameter than said trailing suture.

6. The graft attachment device of claim 1 in which said elongated body is a rectangular, bar-shaped member with rounded longitudinal edges and curved end faces.

7. The graft attachment device of claim 1 in which said sling member has a width of about one-quarter inch.

8. A graft attachment device for attaching an anterior cruciate ligament graft to a bone wherein a passage is drilled through the bone for attachment thereto, comprising:

a graft connection element comprising a sling member having a width sufficient to carry the graft during and after implantation;

an elongated body sized to pass through the passage in the bone and having an upper surface, a lower surface, a leading end, and a trailing end, each said end having a hole defined by said elongated body configured to carry a filament, a portion of said body disposed between said hole in said leading end and said hole in said trailing end being configured for attaching to said body the graft connection element and enabling said body to rotate relative to the graft from an initial insertion position, along an axis substantially parallel to the graft, to a final fixation position transverse to the graft to secure the graft relative to the bone; and filament threaded through said hole in said leading end and said hole in said trailing end.

9. The graft attachment device of claim 8 in which said sling member is a loop of polyester tape material.

10. The graft attachment device of claim 9 in which said portion of said body includes two adjacent openings defined in said elongated body.

11. The graft attachment device of claim 10 in which said sling member has a width of about one-quarter inch.

* * * * *